United States Patent [19]

Sullivan et al.

[11] Patent Number: 6,124,489
[45] Date of Patent: Sep. 26, 2000

[54] PREPARATION OF BIS ARYL CYCLOPENTADIENYL GROUP IVA METAL DIHALIDES

[75] Inventors: Jeffrey M. Sullivan; Roustam Gareyev, both of Loveland, Colo.

[73] Assignee: Boulder Scientific Company, Mead, Colo.

[21] Appl. No.: 09/382,195

[22] Filed: Aug. 23, 1999

[51] Int. Cl.⁷ .................................. C07F 17/00; C07F 7/00
[52] U.S. Cl. ........................... 556/53; 502/103; 502/117; 520/160; 520/943
[58] Field of Search ............................... 556/53; 502/103, 502/117; 526/160, 943

[56] References Cited

U.S. PATENT DOCUMENTS 5,279,999  1/1994  DeBoer et al. ........................ 502/117

OTHER PUBLICATIONS

Erker et al., Chem. Ber., vol. 124, pp. 1301–1310, 1991.

*Primary Examiner*—Porfirio Nazario-Gonzalez
*Attorney, Agent, or Firm*—Edward S. Irons

[57] ABSTRACT

Production of aryl cyclopentadienyl Group IVA metal dihalides by dehydrogenation of a substituted or unsubstituted bis-(cyclohexenylcyclopentadienyl) Group IVA metal dihalide is described.

7 Claims, No Drawings

PREPARATION OF BIS ARYL CYCLOPENTADIENYL GROUP IVA METAL DIHALIDES

FIELD OF THE INVENTION

This invention relates to aryl cyclopentadienyl Group IVA metal dihalides. More particularly, the invention relates to the preparation of bis-phenylcyclopentadienyl zirconium dichloride.

BACKGROUND OF THE INVENTION

U.S. Pat. No. 5,279,999 describes the synthesis of various bis-aryl cyclopentadienyl Group IVA metal dihalides. The adduct of an aryl lithium and cyclopenteneone is treated with an acid to obtain the arylcyclopentadiene which is deprotonated and reacted with a Group IVA metal tetrahalide.

A preparation of pentamethylene fulvene:

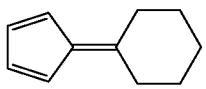

from cyclopentadiene and cyclohexanone in methanol in the presence of pyrrolidine and conversion of the deprotonated fulvene to $[(1\text{-cyclohexen-1-yl})Cp]_2ZrCl_2$ is disclosed in Erker, et al., *Chem. Ber.* (1991) 124:1301–1310.

SUMMARY OF THE INVENTION

Pursuant to this invention, an alkali metal salt of a diisoalkylamide is reacted with a pentamethylene fulvene to produce cyclohexenylcyclopentadiene salt which is further reacted with a Group IVA metal tetrahalide to produce the corresponding bis-cyclopentadienyl Group IVA metal dihalide. Catalytic dehydrogenation of the cyclohexenyl moiety of the bis-cyclopentadienyl Group IVA metal dihalide produces the desired bis-arylcyclopentadienyl Group IVA metal dihalide.

DETAILED DESCRIPTION OF THE INVENTION

In general, the invention may comprise three sequential reactions or steps.

In a first step, a fulvene is produced by reacting cyclohexanone with a cyclopentadiene in medium comprising pyrrolidine and an alkanol:

Reaction 1

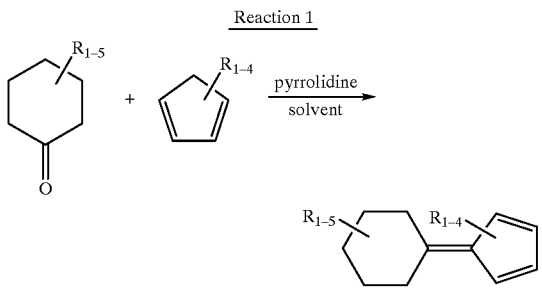

In Reaction 1, each of $R_1$–$R_5$ may be any $C_1$–$C_{10}$ alkyl group substituent at any one or more of the five available ring positions on the cyclohexanone; or any one likewise each of $R_1$–$R_4$ more of the four available ring positions on the cyclopentadiene. Each $R_1$–$R_5$ alkyl group may be the same as or different from any other $R_1$–$R_5$ group. Any non-interfering solvent may be used. One to four carbon atom alkanols are appropriate. Methanol is preferred. The reaction is preferably conducted at a temperature of from 0° C. to 20° C. The relative proportions or mol ratios of the reactants with respect to the cyclopentadiene may be cyclopentadiene:cyclohexanone—from 1:2 to 3:1, cyclohexanone:pyrrolidine—from 3:1 to 1:3.

In a second step, the fulvene product of step 1 is treated with an alkali metal dialkylamide in a non-interfering solvent to provide the corresponding salt as illustrated by Reaction 2:

Reaction 2

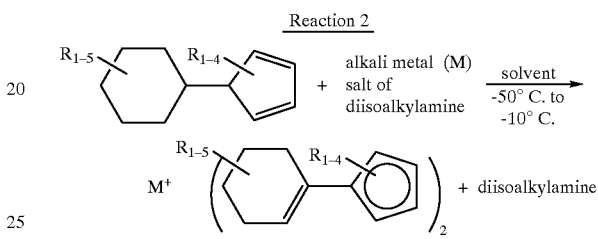

$R_1$–$R_5$ and $R_1$–$R_4$ in Reaction 2 are as defined. M is an alkali metal. Useful non-interfering solvents include ethyl ether and dimethoxy ethane; tetrahydrofuran (THF) is preferred. Reaction 2 is preferably conducted at a temperature of $-50°$ C. to $-10°$ C. A reaction temperature of about $-20°$ C. is preferred. Any alkali metal salt of any diisoalkylamide may be used. Diisoalkylamides having two to six carbon atom alkyl groups are preferred. Although lithium salt is preferred, sodium or potassium salts may be utilized. The relative proportions or mol ratios of diisoalkylamide alkali metal salt with respect to the fulvene is appropriately 1:2 to 2:1. In the preferred practice of the invention, the diisoalkyl diamide salt is added to a solution of the fulvene in a non-interfering solvent, typically THF.

In a third step, the alkali metal salt of cyclohexenyl cyclopentadiene produced in step 2 is treated in THF or another non-interfering solvent with a Group IVA metal tetrahalide $ZX_4$, in which Z is preferably zirconium or titanium, and X is a halogen, preferably chlorine:

Reaction 3

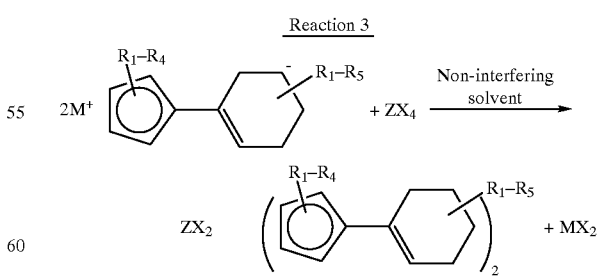

In a fourth step, the cyclohexenyl moiety of the step 3 product is dehydrogenated to provide the desired bis-arylcyclopentadienyl Group IVA metal dihalide:

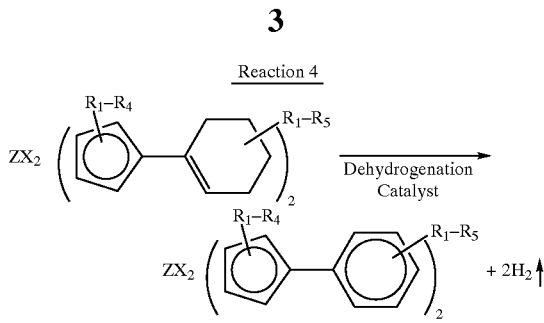

Reaction 4

In Reaction 4, M, Z, R, $R_1$–$R_4$, $R_1$–$R_5$ and X are as defined. The dehydrogenation is appropriately accomplished at a temperature of 150° C. to 300° C. at ambient pressure. Useful dehydrogenation catalysts include rhodium or platinum, on suitable support, e.g., alumina, carbon, or barium sulfate. The preferred catalyst is palladium on activated carbon.

EXEMPLIFICATION OF THE INVENTION

EXAMPLE 1

Pentamethylene fulvene ($C_{11}H_{14}$; FW 146.23)

In a 5-liter flask 1500 ml of methanol, 196 g (2 mol) of cyclohexanone, and 330 g (5 mol) of cyclopentadiene were mixed together. Ice/water cooling was applied and 213 g (3 mol) of pyrrolidine was added as fast as the exotherm allows, keeping the temperature below 25° C. Cooling was removed and the mixture stirred at room temperature for 2 hours. Reaction completion was checked by GC (no cyclohexanone left).

Excess cyclopentadiene, methanol and pyrrolidine were stripped off in vacuum, maintaining as low temperature as possible (the product has a tendency to polymerize when impure). Crude material (dark oil liquid) was dried with sodium sulfate. Yield of crude material is near quantitative. Vacuum distillation (95–100° C. at 1m mercury vacuum) provides a 60% yield of pentamethylene fulvene as a yellow-orange liquid (true color). The rest of the reaction product polymerizes giving very viscous bottoms. Distilled product does not polymerize at room temperature.

NMR (CD2Cl2): 1.81(m) 6H, 274(5) 4H, 6.57(m)2H, 6.66(m)2H.

EXAMPLE 2

Bis(1-(cyclohexen-1-yl)cyclopentadienyl)zirconium dichloride $(C_5H_4(C_6H_9))_2ZrCl_2$, FW 452.58

In a 2-liter flask 128.8 g (0.88 mol) pentamethylene fulvene and 300 ml of THF were mixed. The mixture was cooled to −50 C and 590 ml of 1.5M lithium diisopropyl amide in cyclohexane (0.88 mol) was added over 30 minutes, keeping temperature below −40 C. The mixture was allowed to warm up to room temperature, stirred for 1 hour. Cooled to −50 C again, and 102.8 g (0.44 mol) of zirconium tetrachloride was added over 10 minutes. Allowed to warm up to room temperature and stirred for 1 hour. The solvents were stripped off at pot temperature from 70 C. to 100 C. Toluene (1000 ml) was added to the bottoms, the mixture was heated to 90 C., and solids filtered off. The product precipitates upon cooling as yellow crystalline solid. Filtered, washed with hexane, and dried. Yield 60%. Mother liquors may produce some more product if stripped and let to crystallize. Melting point 159–160 C. NMR(CD2Cl2): 1.64(m)2H, 1.73(m)2H, 2.25(m)4H, 6.21(quintuplet)1H, 6.27(t)2H, 6.40(t)2H.

EXAMPLE 3

Bis(Phenylcyclopentadienyl) Zirconium Dichloride:

In a 100 cc Schlenk flask mixture of 15 g of triethylene glycol dimethyl ether), 15 g of bis-(1-cyclohexen-1-yl) cyclopentadienyl zirconium dichloride as produced in Example 2, and 3 g of palladium on activated carbon) was rapidly heated to reflux (210° to 215° C.). After eight hours of refluxing, the mixture was cooled to room temperature, diluted with 50 ml of hexane, and solids were filtered off. Two crystallization of the solids from hot chlorobenzene yield bis-(phenylcyclopentadienyl) zirconocene dichloride as golden-yellow flaky crystals.

We claim:

1. A method which comprises dehydrogenating the cyclohexenyl moiety of substituted or unsubstituted bis(1-cyclohexen-1-yl)cyclopentadienyl)zirconium dichloride, wherein a dehydrogenation reaction product comprising the corresponding substituted or unsubstituted phenylcyclopentadienyl Group IVA dihalide is produced.

2. A process which comprises:

(i) providing a compound having the formula:

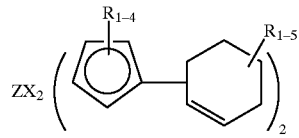

in which Z is a Group IVA metal, X is a halogen, $R_{(1-5)}$ indicates any $C_1$ to $C_{10}$ alkyl group substituent at any one or more of the five available ring substitution positions on the cyclohexenyl ring and $R_1$–$R_4$ indicates any $C_1$ to $C_{10}$ alkyl group substituent at any one or more of the four ring substitution positions on the cyclopentadienyl ring, wherein any one of the $R_{1-5}$ alkyl groups may be the same as or different from any other $R_{1-5}$ alkyl group; and (ii) dehydrogenating said step (i) compound to produce a dehydrogenation reaction product containing a compound having the formula

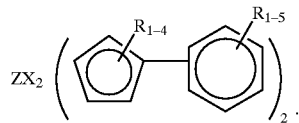

3. A process for producing a bis(phenylcyclopentadienyl) zirconium dichloride which comprises:

(i) providing a bis-(1-(cyclohexen-1-yl)cyclopentadienyl) zirconium dichloride, and (ii) dehydrogenating the cyclohexene-1-yl moiety of said bis(1-(cyclohexan-1-yl)cyclopentadienyl zirconium dichloride, wherein a dehydrogenation reaction mixture containing said bis(phenylcyclopentadienyl) zirconium dichloride is produced.

4. The process of claim 3, wherein said dehydrogenating step (ii) is accomplished with a catalyst comprising palladium on activated carbon.

5. The process of claim 3 or claim 4, wherein said dehydrogenating step (ii) is accomplished in a non-interfering solvent at a temperature of about 150° C. to about 300° C.

6. The process of claim 3, wherein said dehydrogenating step (ii) is accomplished at reflux in a triethylene glycol dimethyl ether solvent.

7. The process of claim 3 or claim 4 further comprising separating said phenylcyclopentadienyl zirconium dichloride from said dehydrogenation reaction mixture.

* * * * *